(12) United States Patent
Kim et al.

(10) Patent No.: US 12,721,672 B2
(45) Date of Patent: Sep. 1, 2026

(54) ELECTROSURGICAL DEVICE, IMPEDANCE MEASURING DEVICE OF THE ELECTROSURGICAL DEVICE, ENERGY CONTROL METHOD FOR TISSUE COAGULATION, AND IMPEDANCE MEASURING METHOD

(71) Applicant: INDUSTRY-UNIVERSITY COOPERATION FOUNDATION HANYANG UNIVERSITY ERICA CAMPUS, Ansan-si (KR)

(72) Inventors: Jung Hyun Kim, Ansan-si (KR); Sungmin Kim, Ansan-si (KR); Sungwoon Hwang, Ansan-si (KR); ByeongCheol Yoon, Ansan-si (KR); Seokmin Lee, Ansan-si (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 281 days.

(21) Appl. No.: 18/701,931

(22) PCT Filed: Jan. 9, 2023

(86) PCT No.: PCT/KR2023/000353

§ 371 (c)(1),
(2) Date: Apr. 17, 2024

(87) PCT Pub. No.: WO2023/163370

PCT Pub. Date: Aug. 31, 2023

(65) Prior Publication Data

US 2025/0221760 A1 Jul. 10, 2025

(30) Foreign Application Priority Data

Feb. 22, 2022 (KR) ........................ 10-2022-0022639

(51) Int. Cl.
*A61B 5/0537* (2021.01)
*A61B 18/12* (2006.01)
(Continued)

(52) U.S. Cl.
CPC .......... *A61B 18/148* (2013.01); *A61B 5/0537* (2013.01); *A61B 18/14* (2013.01);
(Continued)

(58) Field of Classification Search
CPC .......... A61B 2018/1286; A61B 18/148; A61B 2018/00589; A61B 2018/00607;
(Continued)

(56) References Cited

U.S. PATENT DOCUMENTS 10,476,464 B2 * 11/2019 Rambaud ............. H03H 7/0115
2014/0167740 A1 * 6/2014 Gilbert ................. G01R 15/181 324/127

(Continued)

FOREIGN PATENT DOCUMENTS

JP 08229050 A 9/1996
JP 2005000224 A * 1/2005

(Continued)

*Primary Examiner* — Joanne M Rodden
*Assistant Examiner* — Dana Stumpfoll
(74) *Attorney, Agent, or Firm* — NKL Law; Jae Youn Kim

(57) ABSTRACT

It relates to an electrosurgical device, an impedance measuring device of the electrosurgical device, an energy control method for tissue coagulation, and an impedance measuring method, the electrosurgical device is comprised of an instrument for surgery on a target tissue, a processor configured to control energy supply to the instrument and an impedance measurement unit configured to measure an impedance of the target tissue, wherein the processor is further configured to if the impedance measured by the impedance measurement unit exceeds a first reference value, stop the energy
(Continued)

supply to the instrument during a stop period, resume the energy supply to the instrument after the stop period has elapsed, and determine a coagulation state based on the impedance of the target tissue measured after the resumption of the energy supply by the impedance measurement unit.

8 Claims, 10 Drawing Sheets

(51) Int. Cl.
*A61B 18/14* (2006.01)
*A61B 18/00* (2006.01)

(52) U.S. Cl.
CPC ............... *A61B 2018/00589* (2013.01); *A61B 2018/00607* (2013.01); *A61B 2018/00642* (2013.01); *A61B 2018/00666* (2013.01); *A61B 2018/00684* (2013.01); *A61B 2018/00702* (2013.01); *A61B 2018/00708* (2013.01); *A61B 2018/00827* (2013.01); *A61B 2018/00875* (2013.01); *A61B 2018/00892* (2013.01); *A61B 18/1233* (2013.01)

(58) Field of Classification Search
CPC ........... A61B 2018/00702; A61B 2018/00827; A61B 2018/00875; A61B 2018/00892; A61B 2018/00642; A61B 2018/00666; A61B 2018/00708; A61B 18/1233; A61B 5/0537; A61B 18/14; A61B 2018/00684; A61B 2018/00898
See application file for complete search history.

(56) References Cited

U.S. PATENT DOCUMENTS

| | | | | |
|---|---|---|---|---|
| 2015/0094708 | A1* | 4/2015 | Sartor .................... | A61B 18/14 606/34 |
| 2015/0282863 | A1* | 10/2015 | Heckel ............... | A61B 18/1206 700/287 |
| 2016/0066978 | A1 | 3/2016 | Keller et al. | |

FOREIGN PATENT DOCUMENTS

| | | | |
|---|---|---|---|
| JP | 2018511287 | A | 4/2018 |
| KR | 20000005488 | A | 1/2000 |
| KR | 20130095444 | A | 8/2013 |
| KR | 20170099023 | A | 8/2017 |
| KR | 20180123005 | A | 11/2018 |
| KR | 20190086454 | A | 7/2019 |
| KR | 20190102437 | A | 9/2019 |
| KR | 102177375 | B1 | 11/2020 |
| WO | 2021250116 | A1 | 12/2021 |

* cited by examiner

Duty →

Current ↓

| | 12 | 13 | 14 | 15 | 16 | 17 | 18 | 19 | 20 | 21 | 22 |
|---|---|---|---|---|---|---|---|---|---|---|---|
| 1.5 | 45 | 57 | 68 | 81 | 91 | 99 | 107 | 116 | 125 | 136 | 150 |
| 1.6 | 51 | 57 | 68 | 81 | 91 | 99 | 107 | 116 | 125 | 136 | 150 |
| 1.7 | 59 | 73 | 76 | 81 | 91 | 99 | 107 | 116 | 125 | 136 | 150 |
| 1.8 | 62 | 76 | 83 | 91 | 91 | 99 | 107 | 116 | 125 | 136 | 150 |
| 1.9 | 66 | 79 | 91 | 101 | 103 | 109 | 107 | 116 | 125 | 136 | 150 |
| 2 | 69 | 81 | 95 | 111 | 114 | 118 | 121 | 128 | 125 | 136 | 150 |
| 2.1 | 65 | 84 | 99 | 115 | 126 | 128 | 136 | 141 | 143 | 150 | 150 |
| 2.2 | 61 | 80 | 104 | 119 | 132 | 137 | 150 | 153 | 160 | 164 | 164 |
| 2.3 | 57 | 75 | 108 | 122 | 137 | 142 | 155 | 166 | 178 | 178 | 179 |
| 2.4 | 53 | 71 | 112 | 126 | 143 | 147 | 161 | 170 | 184 | 192 | 193 |
| 2.5 | 47 | 66 | 103 | 130 | 148 | 152 | 166 | 176 | 190 | 198 | 207 |
| 2.6 | 41 | 62 | 94 | 122 | 143 | 156 | 172 | 181 | 196 | 204 | 214 |
| 2.7 | 35 | 57 | 84 | 114 | 138 | 161 | 177 | 186 | 202 | 211 | 220 |
| 2.8 | 35 | 52 | 75 | 106 | 133 | 166 | 182 | 191 | 208 | 217 | 227 |
| 2.9 | 35 | 47 | 69 | 98 | 129 | 171 | 188 | 197 | 214 | 223 | 234 |
| 3 | 35 | 42 | 63 | 90 | 124 | 160 | 193 | 202 | 220 | 229 | 240 |
| 3.1 | 35 | 42 | 56 | 82 | 119 | 149 | 183 | 194 | 226 | 236 | 247 |
| 3.2 | 35 | 42 | 50 | 74 | 114 | 137 | 172 | 186 | 218 | 242 | 254 |
| 3.3 | 35 | 42 | 50 | 66 | 109 | 126 | 162 | 178 | 209 | 248 | 260 |
| 3.4 | 35 | 42 | 50 | 58 | 95 | 115 | 152 | 171 | 201 | 237 | 267 |
| 3.5 | 35 | 42 | 50 | 58 | 82 | 106 | 141 | 163 | 192 | 226 | 258 |
| 3.6 | 35 | 42 | 50 | 58 | 68 | 97 | 131 | 155 | 184 | 215 | 248 |
| 3.7 | 35 | 42 | 50 | 58 | 68 | 87 | 120 | 147 | 175 | 204 | 239 |
| 3.8 | 35 | 42 | 50 | 58 | 68 | 78 | 110 | 135 | 167 | 193 | 229 |
| 3.9 | 35 | 42 | 50 | 58 | 68 | 78 | 99 | 123 | 158 | 182 | 220 |
| 4 | 35 | 42 | 50 | 58 | 68 | 78 | 88 | 111 | 146 | 171 | 210 |
| 4.1 | 35 | 42 | 50 | 58 | 68 | 78 | 88 | 99 | 134 | 158 | 201 |
| 4.2 | 35 | 42 | 50 | 58 | 68 | 78 | 88 | 99 | 121 | 144 | 191 |
| 4.3 | 35 | 42 | 50 | 58 | 68 | 78 | 88 | 99 | 109 | 131 | 159 |
| 4.4 | 35 | 42 | 50 | 58 | 68 | 78 | 88 | 99 | 109 | 117 | 126 |

Duty →

Current ↓

| | 12 | 13 | 14 | 15 | 16 | 17 | 18 | 19 | 20 | 21 | 22 |
|---|---|---|---|---|---|---|---|---|---|---|---|
| 1.5 | 100 | 100 | 100 | 100 | 100 | 100 | 100 | 100 | 100 | 100 | 100 |
| 1.6 | 75 | 100 | 100 | 100 | 100 | 100 | 100 | 100 | 100 | 100 | 100 |
| 1.7 | 50 | 50 | 83 | 100 | 100 | 100 | 100 | 100 | 100 | 100 | 100 |
| 1.8 | 40 | 43 | 67 | 83 | 100 | 100 | 100 | 100 | 100 | 100 | 100 |
| 1.9 | 30 | 35 | 50 | 67 | 83 | 88 | 100 | 100 | 100 | 100 | 100 |
| 2 | 20 | 28 | 44 | 50 | 67 | 75 | 83 | 128 | 100 | 100 | 100 |
| 2.1 | 18 | 20 | 38 | 44 | 50 | 63 | 67 | 75 | 83 | 88 | 100 |
| 2.2 | 15 | 18 | 32 | 38 | 43 | 50 | 50 | 63 | 67 | 75 | 88 |
| 2.3 | 13 | 16 | 26 | 32 | 35 | 46 | 46 | 50 | 50 | 63 | 75 |
| 2.4 | 10 | 14 | 20 | 26 | 25 | 41 | 43 | 46 | 46 | 50 | 63 |
| 2.5 | 8 | 12 | 18 | 20 | 20 | 37 | 39 | 41 | 43 | 47 | 50 |
| 2.6 | 7 | 10 | 15 | 18 | 19 | 33 | 35 | 37 | 39 | 43 | 47 |
| 2.7 | 5 | 9 | 13 | 16 | 18 | 29 | 31 | 33 | 35 | 40 | 43 |
| 2.8 | 5 | 8 | 10 | 14 | 16 | 24 | 28 | 29 | 31 | 37 | 40 |
| 2.9 | 5 | 6 | 9 | 12 | 15 | 20 | 24 | 24 | 28 | 33 | 37 |
| 3 | 5 | 5 | 8 | 10 | 14 | 18 | 20 | 20 | 24 | 30 | 33 |
| 3.1 | 5 | 5 | 6 | 9 | 13 | 16 | 18 | 19 | 20 | 27 | 30 |
| 3.2 | 5 | 5 | 5 | 8 | 11 | 14 | 17 | 17 | 19 | 23 | 27 |
| 3.3 | 5 | 5 | 5 | 6 | 10 | 12 | 15 | 16 | 18 | 20 | 23 |
| 3.4 | 5 | 5 | 5 | 5 | 8 | 10 | 13 | 14 | 16 | 19 | 20 |
| 3.5 | 5 | 5 | 5 | 5 | 7 | 9 | 12 | 13 | 15 | 17 | 19 |
| 3.6 | 5 | 5 | 5 | 5 | 5 | 8 | 10 | 11 | 14 | 16 | 18 |
| 3.7 | 5 | 5 | 5 | 5 | 5 | 6 | 9 | 10 | 13 | 14 | 16 |
| 3.8 | 5 | 5 | 5 | 5 | 5 | 5 | 8 | 9 | 11 | 13 | 15 |
| 3.9 | 5 | 5 | 5 | 5 | 5 | 5 | 6 | 8 | 10 | 11 | 14 |
| 4 | 5 | 5 | 5 | 5 | 5 | 5 | 5 | 6 | 9 | 10 | 13 |
| 4.1 | 5 | 5 | 5 | 5 | 5 | 5 | 5 | 5 | 8 | 9 | 11 |
| 4.2 | 5 | 5 | 5 | 5 | 5 | 5 | 5 | 5 | 6 | 8 | 10 |
| 4.3 | 5 | 5 | 5 | 5 | 5 | 5 | 5 | 5 | 5 | 6 | 8 |
| 4.4 | 5 | 5 | 5 | 5 | 5 | 5 | 5 | 5 | 5 | 5 | 5 |

ELECTROSURGICAL DEVICE, IMPEDANCE MEASURING DEVICE OF THE ELECTROSURGICAL DEVICE, ENERGY CONTROL METHOD FOR TISSUE COAGULATION, AND IMPEDANCE MEASURING METHOD

TECHNICAL FIELD

The present invention relates to an electrosurgical device, an impedance measuring device of the electrosurgical device, an energy control method for tissue and an impedance measuring method.

BACKGROUND ART

An electric surgical instrument is a medical instrument which applies electrical energy to an affected area and locally heats the affected area to simultaneously perform an incision of a target tissue and coagulation of a target tissue and surrounding tissue, and is currently widely used because the surgical instrument minimizes bleeding by coagulating the tissue while an incision of the tissue is made to greatly shorten a surgical operation time. When operating an electrosurgical instrument, appropriate energy must be supplied to the target tissue. If excessive energy is transferred to the target tissue, thermal energy may be diffused into surrounding tissue, causing thermal damage to the surrounding tissue, and also carbonized components of tissue may be cohered to a jaw provided at an end of the surgical instrument, causing secondary tissue destruction. Conversely, if insufficient energy is transferred to the target tissue, the target tissue does not coagulate properly, making hemostasis difficult.

Meanwhile, the electrosurgical instrument mainly uses electric energy of a high frequency, because human muscles and nerves do not react with a current of a high frequency of 20 kHz or more, and energy transfer to a subcutaneous tissue layer other than a surgical site is controlled by a skin effect as the frequency is higher, and efficient energy penetration into the inside of the tissue and effective heating from the inside of the tissue are possible. However, as the frequency increases, the influence of the parasitic inductance and the parasitic capacitance on the electrosurgical instrument increases, and the parasitic resistance component due to the skin effect has a great influence on the operation of the electrosurgical instrument, which makes the operation of the electrosurgical instrument based on high frequency electric energy quite difficult.

DISCLOSURE

Technical Problems

An object of the present invention is to provide an electrosurgical device and an energy control method for tissue coagulation, which can appropriately control energy supply so that a target tissue or surrounding tissue of the target tissue is not damaged by heat while the target tissue is properly coagulated during a surgical procedure.

Another object of the present invention is to provide an impedance measuring device and method of the electrosurgical device which can appropriately measure the impedance of a target tissue or surrounding tissue in a high frequency band.

Technical Solution

In order to solve the above problems, an electrosurgical device, an impedance measuring device of the electrosurgical device, an energy control method for tissue coagulation, and an impedance measuring method are provided.

An electrosurgical device comprises an instrument for surgery on a target tissue, a processor configured to control energy supply to the instrument and an impedance measurement unit configured to measure an impedance of the target tissue, wherein the processor is further configured to if the impedance measured by the impedance measurement unit exceeds a first reference value, stop the energy supply to the instrument during a stop period, resume the energy supply to the instrument after the stop period has elapsed, and determine a coagulation state based on the impedance of the target tissue measured after the resumption of the energy supply by the impedance measurement unit.

The processor is configured to control the energy supply to the instrument using at least one lookup table.

The processor is further configured to determine a moisture amount of surrounding tissues of the target tissue by using the impedance of the target tissue measured by the impedance measurement unit after the energy supply is resumed, and determine a coagulation state based on the moisture amount.

The processor is configured to block the energy supply to the instrument when a total surgical time exceeds a reference time.

An electrosurgical device further comprises a voltage-current measuring unit comprising a capacitor, an isolation transformer connected to the capacitor and configured to output a first voltage signal corresponding to a voltage, a PCB Rogowski coil installed adjacent to a conducting wire to which the capacitor is connected and an active integrator connected to the PCB Rogowski coil and configured to correct a phase of the active integrator to output a second voltage signal corresponding to a current.

An electrosurgical device further comprises an impedance measurement unit configured to receive the first voltage signal and the second voltage signal, to obtain impedance based on the first voltage signal and the second voltage signal, and to transmit the impedance to the processor.

The impedance measurement unit comprises a first active low-pass filter configured to remove a harmonic component of the first voltage signal, a first multiplication processor configured to perform a multiplication process on an output of the first active low-pass filter, a first passive low-pass filter configured to obtain a direct current component corresponding to a voltage from a result of the first multiplication processor, a second active low-pass filter configured to remove a harmonic component of the second voltage signal, a second multiplication processor configured to perform a multiplication process on an output of the second active low-pass filter, a second passive low-pass filter configured to obtain a direct current component corresponding to a current from a result of the second multiplication processor, a third multiplication processor configured to perform a multiplication process on an output of the first active low-pass filter and the second active low-pass filter, a third passive low-pass filter configured to obtain a direct current component corresponding to a phase from a result of the third multiplication processor and a result acquisition unit configured to determine a voltage, a current, and a phase based on a direct current component corresponding to the voltage, a direct current component corresponding to the current, and a direct current component corresponding to the phase, and to determine an impedance based on the voltage, the current, and the phase.

An impedance measuring device comprises a first active low-pass filter configured to remove a harmonic component of a first voltage signal obtained in correspondence to a voltage of a target tissue, a first multiplication processor configured to perform a multiplication process on an output of the first active low-pass filter, a first passive low-pass filter configured to obtain a direct current component corresponding to the voltage from a processing result of the first multiplication processor, a second active low-pass filter configured to remove a harmonic component of a second voltage signal obtained in correspondence to a current of the target tissue, a second multiplication processor configured to perform a multiplication process on an output of the second active low-pass filter, a second passive low-pass filter configured to obtain a direct current component corresponding to the current from a processing result of the second multiplication processor, a third multiplication processor configured to perform a multiplication process on an output of the first active low-pass filter and the second active low-pass filter, a third passive low-pass filter configured to obtain a direct current component corresponding to a phase from a processing result of the third multiplication processor and a result acquisition unit configured to determine a voltage, a current, and a phase based on a DC component corresponding to the voltage, a DC component corresponding to the current, and a DC component corresponding to the phase, and to determine an impedance based on the voltage, the current, and the phase.

An electrosurgical method comprises supplying energy to an instrument for surgery of a target tissue, measuring an impedance of the target tissue, stopping the energy supply to the instrument during a stopping period when the impedance measured by the impedance measuring unit exceeds a first reference value, resuming the energy supply to the instrument after the stopping period has elapsed and determining a coagulation state based on the impedance of the target tissue measured after resuming the energy supply.

An impedance measuring method comprises removing a harmonic component from each of a first voltage signal obtained corresponding to a voltage of a target tissue and a second voltage signal obtained corresponding to a current of the target tissue, performing multiplication on each of the first voltage signal from which the harmonic component is removed and the second voltage signal from which the harmonic component is removed, obtaining a direct current component corresponding to a voltage and a direct current component corresponding to a current from each multiplication result, performing multiplication using both the first voltage signal from which the harmonic component is removed and the second voltage signal from which the harmonic component is removed, obtaining a direct current component corresponding to a phase from a multiplication result using both the first voltage signal from which the harmonic component is removed and the second voltage signal from which the harmonic component is removed, determining a voltage, a current, and a phase based on the direct current component corresponding to the voltage, the direct current component corresponding to the current, and the direct current component corresponding to the phase and determining impedance based on the voltage, the current, and the phase.

Advantageous Effects

According to the electrosurgical device and an energy control method for tissue coagulation described above, the energy supply to a target tissue and the like is appropriately controlled in a surgical process, so that the target tissue or surrounding tissue of the target tissue is not damaged by heat while the target tissue is properly coagulated.

According to the electrosurgical device and an energy control method for tissue coagulation described above, it is possible to obtain an advantage that the electrosurgical device may be operated based on high frequency energy.

According to the electrosurgical device and an energy control method for tissue coagulation described above, it is possible to obtain an advantage that determining the high-frequency energy required for tissue coagulation based on the impedance measured in real time and applying it to the tissue.

According to the impedance measuring device and the impedance measuring method of the electrosurgical device described above, the impedance of the target tissue or surrounding tissue in the high frequency band may be appropriately measured, and the energy supply to the target tissue or the like may be more appropriately controlled based on the measured impedance.

According to the impedance measuring device and impedance measurement method of the electrosurgical device described above, since the conventional pulse lock loop (PLL)-based calculation process is performed through analog circuits, it is possible to measure the impedance in the high frequency band that could not be measured due to the sampling frequency limit of the conventional digital signal processor (DSP).

According to the impedance measuring device and impedance measurement method of the electrosurgical device described above, impedance measurement is possible without deteriorating the performance of the electrical surgical device by minimizing electrical interference with the electrical surgical device.

DESCRIPTION OF DRAWINGS

FIG. 3*b* and FIG. 3*c* are diagrams of a lookup table of output and impedance.

BEST MODE

Figure 1:
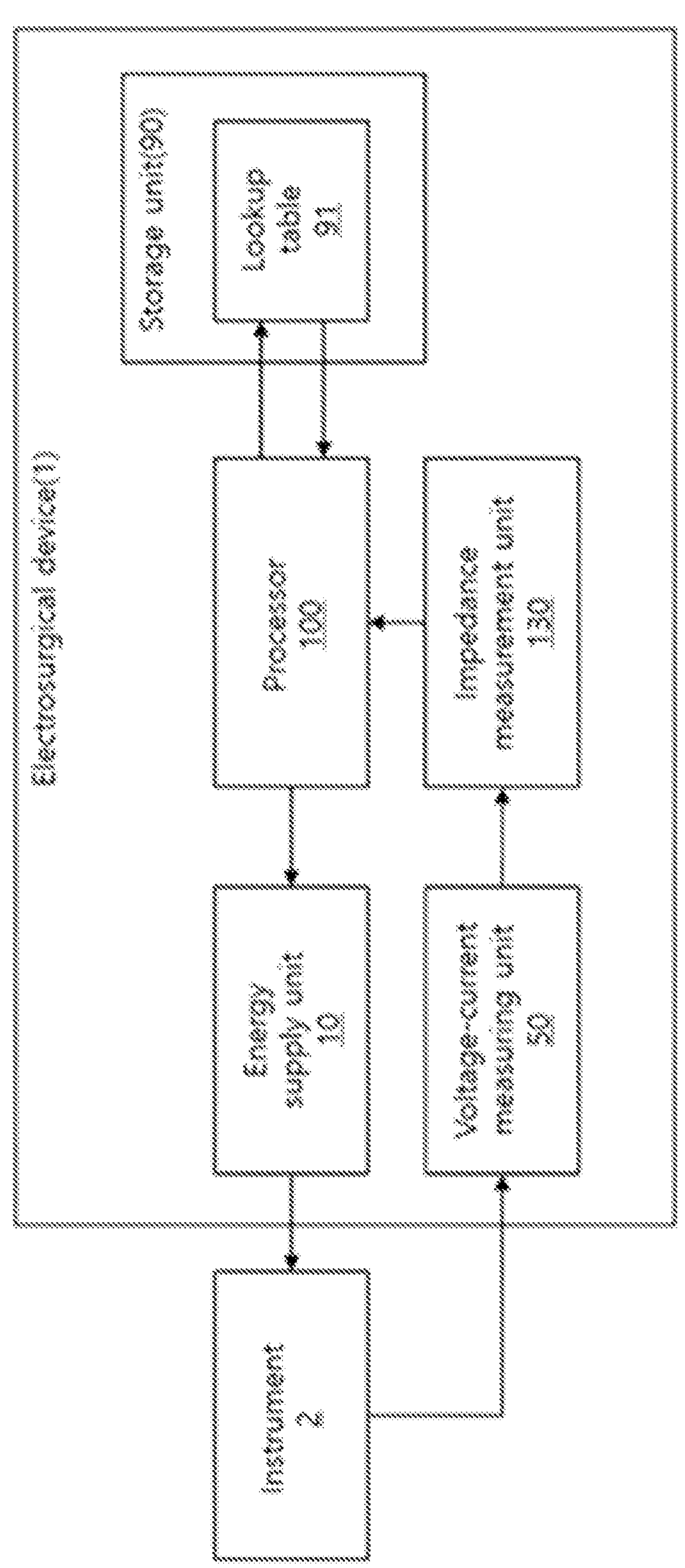
FIG. 1 is a block diagram of an embodiment of an electrosurgical device.

Throughout the specification, unless otherwise indicated, identical reference numerals in the different parts denote the same component. The term “unit” used herein with respect to various features may be implemented in software and/or hardware, wherein, according to embodiments, a single “unit” may be implemented as one physical or logical component, or multiple “unit” may be implemented as one physical or logical component, or one “unit” may be implemented as multiple physical or logical components. When any part is described as being connected to another part throughout the specification, this may indicate that the parts are physically and/or electrically connected to each other. Furthermore, when one part is said to include another part, it does not necessarily exclude any other part besides the other part unless expressly stated otherwise, and it may include additional parts depending on the designer's choice. Expressions such as "first to Nth (where N is a natural number greater than or equal to 1)" are used to distinguish at least one part from other parts, and unless expressly stated otherwise, they do not necessarily imply sequentiality. Additionally, singular expressions may include plural expressions unless contextually indicated otherwise.

Hereinafter, an embodiment of an electrosurgical device will be described with reference to FIGS. 1 to 3*b*.

FIG. 1 is a block diagram of an embodiment of an electrosurgical device.

Referring to FIG. 1, the electrosurgical device 1 may include an energy supply unit 10, a voltage-current measuring unit 50, a processor 100, and an impedance measurement unit 130, and may further include a storage unit 90, if necessary.

The energy supply unit 10 may be physically or electrically connected to at least one instrument 2 (which may be referred to as a handpiece and may include a plurality of electrodes electrically connected to the electrosurgical device 1) for surgery on a tissue (hereinafter, referred to as a target tissue) to be electrosurgical, and may supply electrical energy to the connected instrument 2. The instrument 2 is used to incise a target tissue or coagulate a cut surface of the incised tissue or the periphery thereof. Specifically, when an electrical signal having a specific waveform and a specific frequency is provided to the instrument 2 by the energy supply unit 10 in a state in which the instrument 2 is in contact with or is close to a specific portion, electrical energy is concentrated on the portion in contact with the instrument 2 and the corresponding portion is heated, and accordingly, the corresponding portion may be incised, coagulated, and hemostasis. The operation of the energy supply unit 10 may be controlled by the processor 100.

The voltage-current measuring unit 50 may acquire information about voltage and/or current to measure the impedance and transmit the information to the impedance measurement unit 130. Since the impedance may be given by Equation 1 below, the impedance of the target tissue may be determined when information about the input voltage V and/or the input current provided from the instrument 2 is given.

$$Z = \frac{V}{I} \angle \phi \quad \text{[Equation 1]}$$

Here, Z is impedance, V is voltage, and I is current. The voltage-current measuring unit 50 will be described in detail later.

The storage unit 90 may temporarily or non-temporarily store at least one piece of data required for the operation of the processor 100, the impedance measurement unit 130, or the like, commands/instructions, and/or a program (which may be referred to as an app, an application, software, or the like) specifically designed for energy control, impedance measurement, or the like. For example, the storage unit 90 may store at least one lookup table 91 for controlling energy delivered to a tissue. The storage unit 90 transfers data or the like required according to a call of the processor 100 or the impedance measurement unit 130 to the processor 100 or the impedance measurement unit 130 so that the processor 100 or the impedance measurement unit 130 performs a predetermined operation. The programs stored in the storage unit 90 may be directly created and stored by a designer, may be transferred from an external memory device, and/or may be obtained or updated through an electronic software distribution network accessible through a wired/wireless communication network. The storage unit 90 may include, for example, at least one of a main memory device and an auxiliary memory device. The main memory device may be implemented using a semiconductor storage medium such as a ROM and/or a RAM, and the auxiliary memory device may be implemented using at least one storage medium such as a flash memory-based memory device (for example, a Solid State Drive (SSD), a Secure Digital (SD) card, or the like), a Hard Disk Drive (HDD), or the like.

Figure 2:
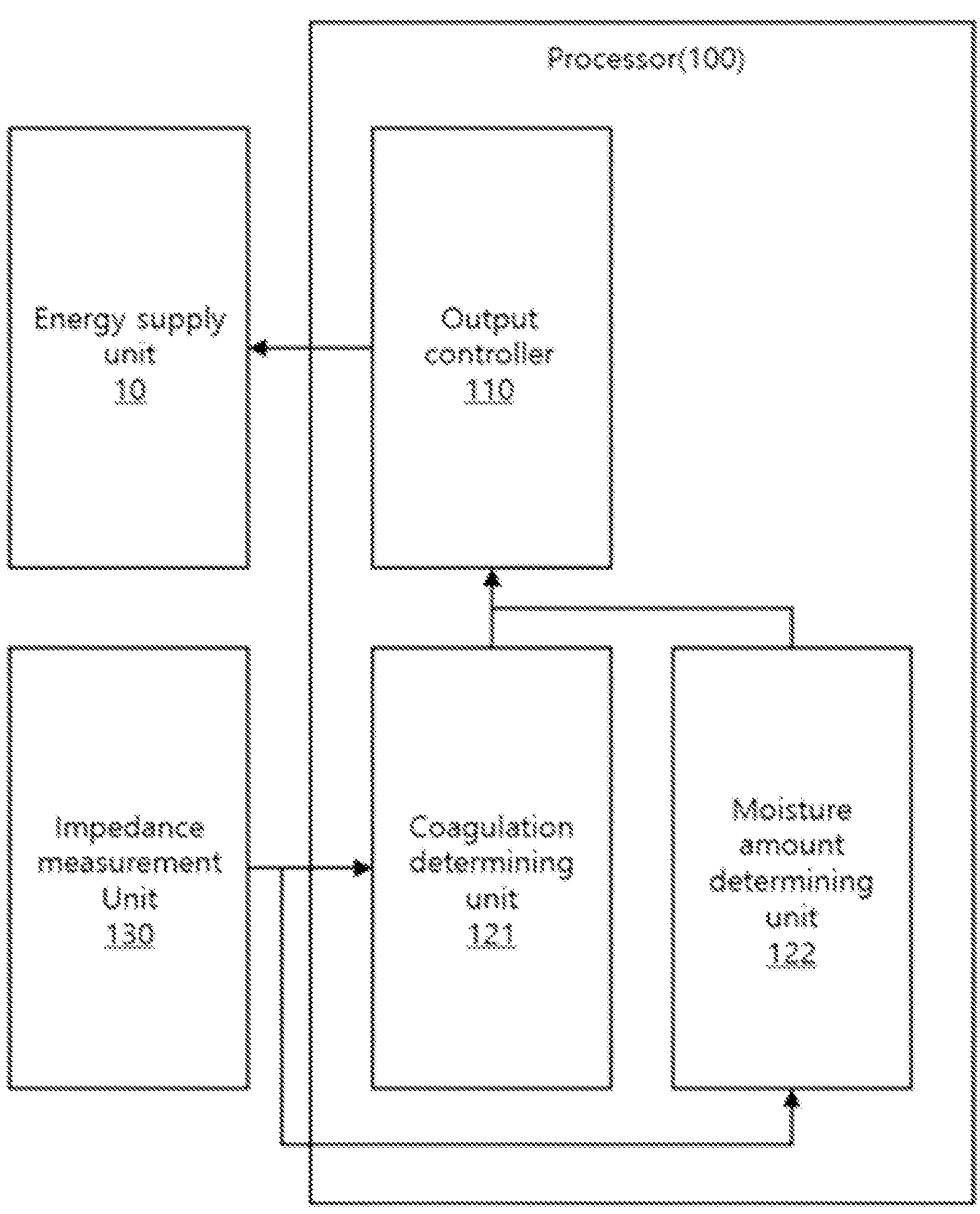
FIG. 2 is a block diagram illustrating an embodiment of a processor.
Figure 3A:
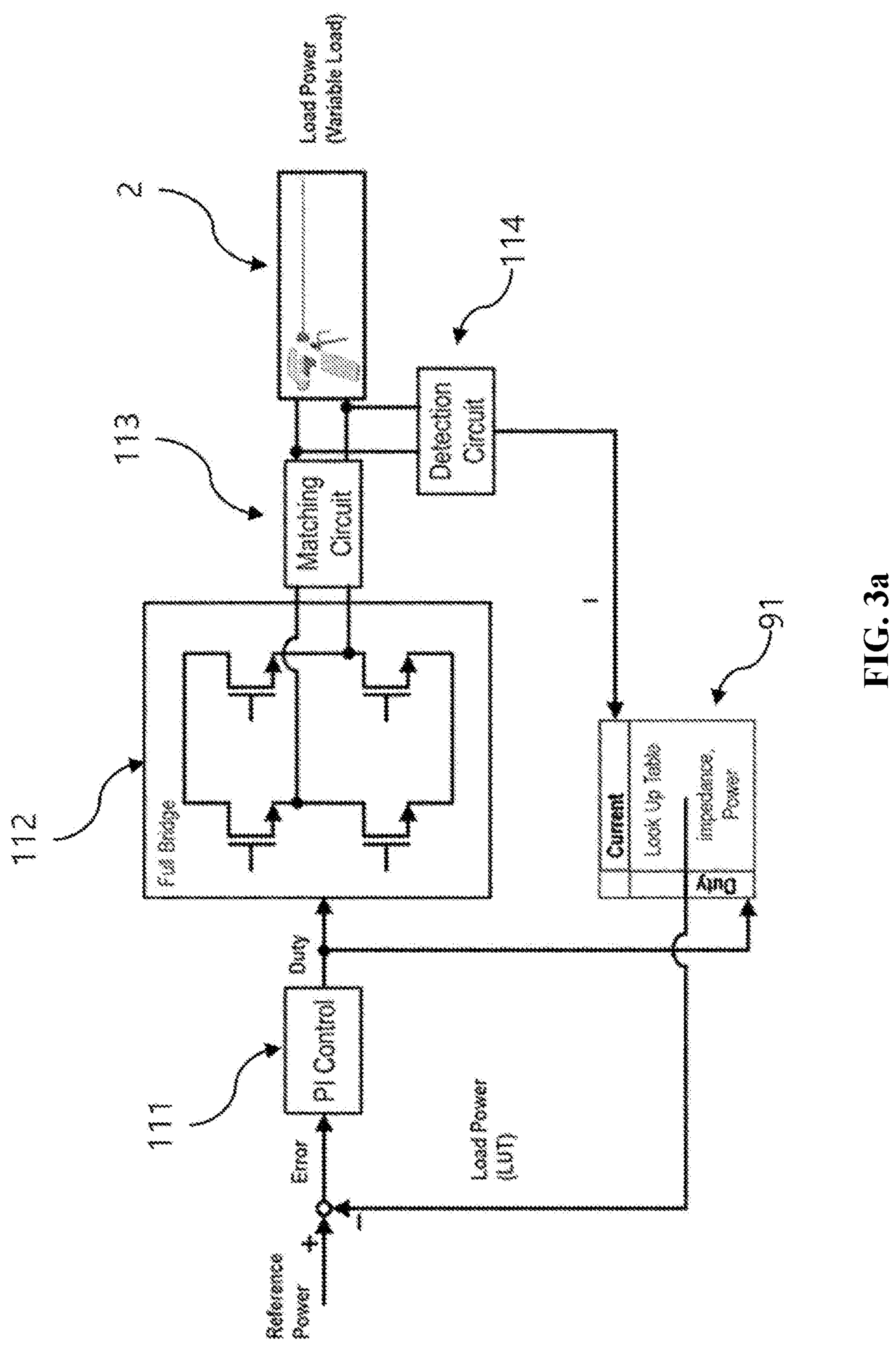
FIG. 3*a* is a diagram illustrating an embodiment of an output controller.

FIG. 2 is a block diagram illustrating an embodiment of a processor, and FIG. 3*a* is a diagram illustrating an embodiment of an output controller. In addition, FIGS. 3*b* and 3*c* are diagrams of a lookup table of output and impedance, and in the diagrams of FIGS. 3*b* and 3*c*, a left column represents current and an upper row represents duty. In FIG. 3*b*, a value of a point at which each column and each row meet each other records an output transferred from a corresponding current and duty to a target tissue, and in FIG. 3*c*, a value of a point at which each column and each row meet each other records an impedance transferred from the target tissue in a corresponding current and duty, and more particularly, a duty of a full bridge converter and an output and impedance transferred from the target tissue through a current output from the instrument 2 are recorded.

The processor 100 may control the energy supply of the energy supply unit 10 to control the supply and stop of an electrical signal applied to the instrument 2, or may adjust the intensity, wavelength, frequency, or the like of the supplied electrical signal. Also, according to an embodiment, the processor 100 may control power supply to the instrument 2 based on the measurement result of the impedance measurement unit 130.

Specifically, as shown in FIG. 2, the processor 100 may include an output controller 110, a coagulation determining unit 121, and a moisture amount determining unit 122.

The output controller 110 may transmit an electrical signal (e.g., a control signal, etc.) to the energy supply unit 10 so that the energy supply unit 10 may supply an electrical signal having a specific wavelength or frequency to the instrument 2 or stop the energy supply to the instrument 2. According to an embodiment, as illustrated in FIGS. 3*a* to 3*c*, the output controller 110 may include a proportional-integral controller (PI controller) 111 configured to output a duty to reduce an error calculated by using reference power and a lookup table 91 (91-1, 91-2), a Full Bridge converter 112 configured to perform a DC-AC conversion based on four rectifications based on the duty output from the PI controller 111, a matching circuit 113 configured to match an input impedance, and a detection circuit 114 configured to detect an impedance and energy observed from the instrument 2.

As the frequency of the electrical energy increases, when a parasitic component (parasitic inductance, parasitic capacitance, etc.) is generated in the instrument 2 due to a skin effect, etc., this greatly affects the overall energy control. In particular, due to the structure of the instrument 2, a large parasitic resistance acts against a low impedance load, and thus the instrument 2 itself consumes a large amount of energy, and accordingly, the energy is not transferred to the target tissue. In other words, the measured energy in the instrument 2 may not be delivered to the tissue depending on the situation, and the ratio may be different. Accordingly, when the instrument 2 is used at a high frequency, the impedance of the target tissue measured by the instrument 2 is not only significantly different from the impedance of the actual load but also does not linearly map. Therefore, for more accurate output control, the output controller 110 may determine the output of the instrument 2 required for the target tissue by referring to the lookup table 91-1 for power as illustrated in FIG. 3*b* and the lookup table 91-2 for impedance as illustrated in FIG. c, based on the current output from the instrument 2 and the duty of the full bridge converter 112, and may control the energy supply unit 10 based on the impedance, and accordingly, a predetermined level of energy may be supplied to the target tissue.

In a general operation process, when a tissue is incised by the instrument 2, not only the incised tissue but also surrounding tissues should be sufficiently coagulated to prevent bleeding at the surgical site. The output controller 110 may control the energy supply to the instrument 2 so that other tissue(s) around the target tissue, as well as the target tissue, may be properly coagulated. To this end, the measured impedance of the target tissue may be used. According to an embodiment, to this end, the output controller 110 may sequentially receive the determination result from the coagulation determining unit 121 and the moisture amount determining unit 122 of the processor 100, and control the energy supplier 10 based on the determination result.

The coagulation determining unit 21 may determine whether the impedance is greater than a predefined reference value (hereinafter, referred to as a first reference value), and may determine whether the impedance of the tissue is suitable for coagulation based on the determination result. For example, the coagulation determining unit 121 receives the impedance from the impedance measurement unit 130, and if the received impedance is greater than the first reference value, transmits a signal corresponding thereto to the output controller 110, and the output controller 110 transmits a control signal to the energy supply unit 10 in response to the transmitted signal so that the energy supply unit 10 stops supplying energy to the instrument 2. The first reference value may be predefined by a designer or a user. The coagulation determining unit 21 may refer to the lookup table 91-2 for impedance in order to perform the above-described operation as needed. The incised target tissue gradually increases in impedance because moisture evaporates and carbonizes during coagulation. However, as described above, when the energy supply to the target tissue is stopped according to the control of the output controller 110, moisture flows into the target tissue from another tissue located around the target tissue, and as the moisture increases, the impedance of the target tissue relatively decreases. The interruption of the energy supply may be performed for a predefined interruption period. Here, the interruption period may be defined based on a time during which sufficient moisture can be supplied to the target tissue, and may be, for example, about 200 ms. When the predefined interruption period has elapsed, the output controller 110 may control the energy supply unit 10 again so that the energy supply unit 10 supplies energy to the instrument 2. In other words, the energy supply to the target tissue is resumed.

Figure 3D:
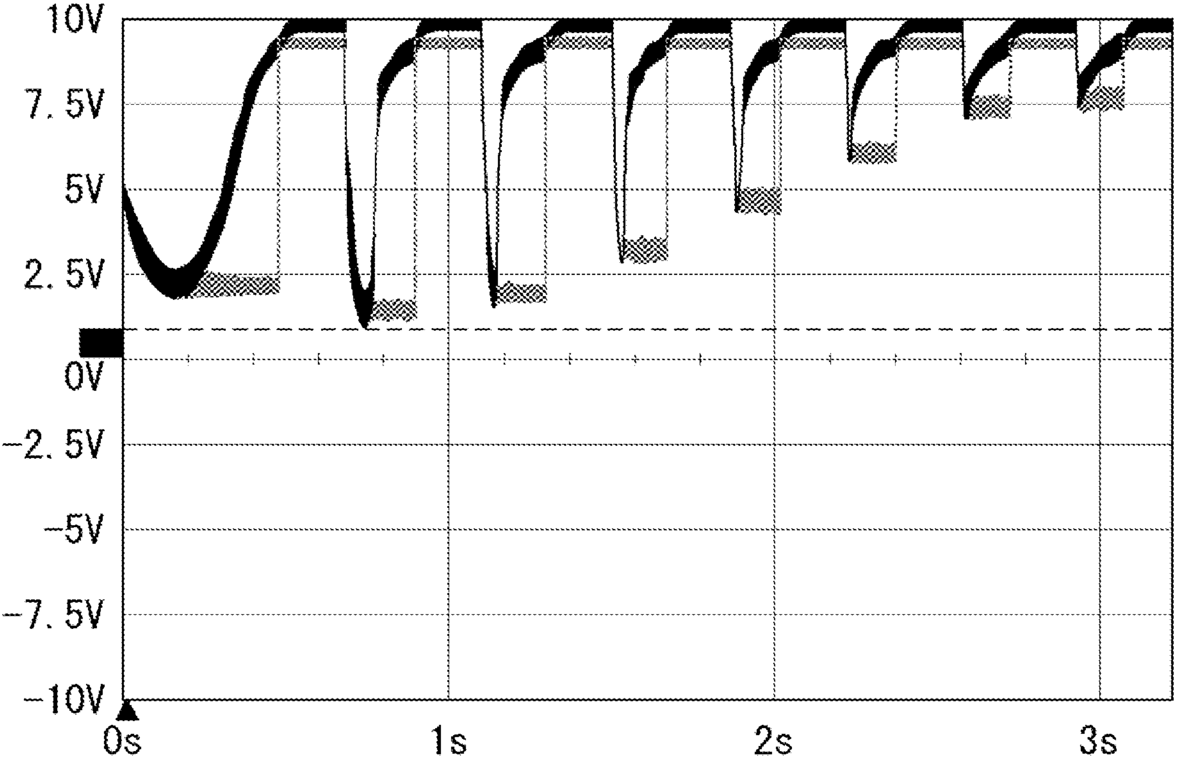
FIG. 3*d* is a graph illustrating real-time tissue impedance and minimum impedance measured in an operation process of a processor.

FIG. 3*d* is a graph illustrating real-time tissue impedance and minimum impedance measured in an operation process of a processor, wherein a blue line corresponds to real-time tissue impedance and a green line corresponds to minimum tissue impedance in each energy application section.

The moisture amount determining unit 122 may allow the output controller 110 to control the energy supply unit 10 according to the determination result of the coagulation determining unit 121, receive the impedance from the impedance measurement unit 130, and predict and determine the moisture amount of the surrounding portion based on the received impedance. According to an embodiment, the moisture amount determining unit 122 may receive the impedance after a predetermined period (for example, an energy supply stop period) has elapsed, may continuously receive the impedance for a predetermined period, and/or may receive the impedance a plurality of times. As described above, when energy is again applied to the target tissue through the instrument 2 after the energy supply is stopped, the impedance of the target tissue is reduced due to the influence of moisture supplied from other surrounding tissues before the energy supply is stopped, as shown in FIG. 3*d*. When such a change in impedance is used, it is possible to determine whether a coagulation state of surrounding tissues in addition to the target tissue is appropriate. That is, when energy is supplied, the impedance of the target tissue is increased by reduction of moisture and carbonization, and when the energy supply is stopped and then resumed, the impedance of the target tissue is relatively low, but gradually increases due to the reduction of moisture and carbonization according to the resumed energy supply. When the energy supply is stopped again and then resumed, the impedance of the target tissue is measured to be low again. However, as moisture flows into the target tissue repeatedly or continuously, the moisture amount of the surrounding tissue is gradually reduced, and the moisture amount flowing into the target tissue is correspondingly reduced. Accordingly, a minimum value of the impedance in a specific energy supply period is gradually increased. According to an embodiment, the moisture amount determining unit 122 may predict the moisture amount of the target tissue and/or the surrounding tissue by using the above points. Specifically, the moisture amount determining unit 122 may obtain a minimum impedance value among the impedance measured in the section in which the energy is applied again and may predict the moisture amount of the target tissue and/or the surrounding tissue based on the obtained impedance. When the moisture amount is predicted, the coagulation state at the corresponding time point can be determined, and the degree of energy application during the entire operation can also be determined. According to an embodiment, the moisture amount determining unit 122 may compare the obtained impedance value (e.g., the minimum impedance) with a predefined reference value (hereinafter, referred to as a second reference value), and when the impedance value is greater than the second reference value, may determine that the moisture amount is small, and may determine that the coagulation state is appropriate. In some embodiments, the moisture amount determining unit 122 may use a lookup table 91-2 about impedance to determine the moisture amount or the coagulation state.

The output controller 110 may control the energy supply unit 10 based on the amount of moisture or the coagulation state determined by the moisture amount determining unit 122. For example, when the moisture amount determining unit 122 determines that the coagulation state is appropriate, the output controller 110 may control the energy supply unit 10 in response to the determination so that energy is no longer supplied to the instrument 2. Accordingly, the surgery may be stopped or terminated. Meanwhile, according to an embodiment, the output controller 110 may measure a time (hereinafter, referred to as a total operation time) elapsed after the start of the surgery by using a clock (not shown), and when the total operation time has elapsed a predetermined reference time (for example, 10 sec), control the energy supply unit 10 in response to the measurement regardless of whether the amount of water is appropriate so that energy is no longer supplied to the instrument 2. This is to prevent situations in which coagulation or moisture inflow does not occur due to other unexpected factors.

The processor 100 may be implemented based on a Central Processing Unit (CPU), a Graphic Processing Unit (GPU), a Micro Controller Unit (MCU), an Application Processor (AP), an Electronic Controlling Unit (ECU), or the like.

Hereinafter, an embodiment of the voltage-current measuring unit 50 will be described with reference to FIG. 4.

Figure 4:
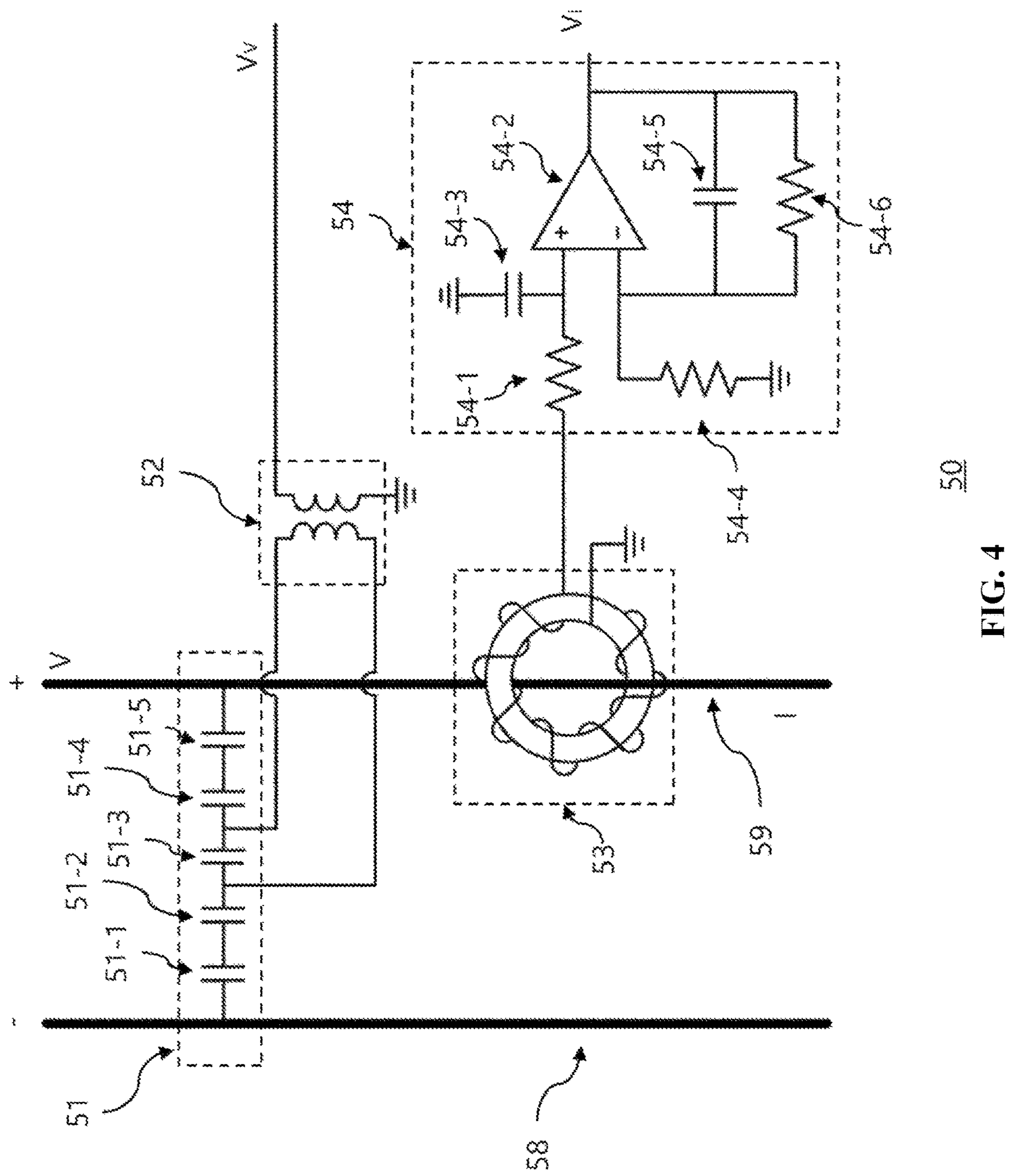
FIG. 4 is a circuit diagram of a voltage-current measuring according to an embodiment.

FIG. 4 is a circuit diagram of a voltage-current measuring according to an embodiment.

As described above, the voltage-current measuring unit 50 may measure the voltage and/or current of the target tissue. Referring to FIG. 4, the voltage-current measuring unit 50 may include at least one capacitor 51, an isolation transformer 52, a PCB Rogowski coil (PCB Rogowski) coil 53, and an active integrator 54.

The at least one capacitor 51 may include a plurality of capacitors 51-1 to 51-5 connected to each other in series. In this case, among a plurality of capacitors, for example, five capacitors 51-1 to 51-5, the first capacitor 51-1 at one end is electrically connected to the conducting wire 58 connected to the negative electrode (−), and the fifth capacitor 51-5 at the other end is electrically connected to the conducting wire 59 connected to the positive electrode (+). The capacitances of the capacitors 51-1 to 51-5 may be the same, may be partially the same, or may be all different. For example, the first capacitor 51-1, the second capacitor 51-2, the fourth capacitor 51-4, and the fifth capacitor 51-5 may have the same capacitance, but the third capacitor 51-3 may have different capacitances. A branch line is formed at one point between the second capacitor 51-2 and the third capacitor 51-3 and at one point between the third capacitor 51-3 and the fourth capacitor 51-4, and the branch line is connected to the isolation transformer 52. In this case, sensitivity for voltage measurement may be determined according to the number of capacitors 51 or capacitance. For example, the sensitivity may be given as the capacitance of the third capacitor 51-3 with respect to the total capacitance of the plurality of capacitors 51-1 to 51-5 as shown in Equation 2 below.

$$\frac{C_2}{4C_1 + C_2} \quad \text{[Equation 2]}$$

In Equation 2, C_1 is capacitance of the first capacitor 51-1, the second capacitor 51-2, the fourth capacitor 51-4, and the fifth capacitor 51-5, and C_2 is capacitance of the third capacitor 51-3. The capacitances C_1 and C_2 of the respective capacitors 51-1 to 51-5 may be determined to have a relatively large impedance with respect to the high-frequency electrical signal in order to prevent performance deterioration of the electrosurgical device 1.

The isolation transformer 52 is provided for insulation and may include a 1:1 transformer, but is not limited thereto. According to an embodiment, the number of coils corresponding to each other in the isolation transformer 52 may be different from each other. The isolation transformer 52 may have one end connected to a line connecting at least two capacitors (51-2 and 51-3, 51-3 and 51-4) and the other end connected to the impedance measurement unit 130 to transmit a voltage signal V_v (hereinafter, referred to as a first voltage signal) corresponding to the input voltage V to the impedance measurement unit 130.

The PCB Rogowski coil 53 may generate an induced voltage and an induced current corresponding to the current I passing through the conducting wire 59 according to the Faraday's law, and transfer the induced current to the active integrator 54. In this case, the transmitted induced current may be a current of which a phase is changed. For example, the PCB Rogowski coil 53 may be formed by winding a coil around a donut-type core, and one end of the coil is connected to the active integrator 54. A conducting wire (59) passes through a center hole of the donut-shaped core. In other words, the PCB Rogowski coil 53 is installed adjacent to the conducting wire 59. Meanwhile, in this case, the sensitivity with respect to the current measurement may be determined through the number of turns of the coil of the PCB Rogowski coil 53 and the radius of the core, and may be determined by further using the sizes of the resistors 54-1 and 54-4 of the active integrator 54 or the capacitance of the capacitor 54-3, if necessary.

The active integrator 54 may receive the induced voltage/current output from the PCB Rogowski coil 53, amendment and recover a phase of the received induced voltage/current, and output a voltage signal V_I (hereinafter, referred to as a second voltage signal) corresponding thereto. The active integrator 54 is electrically connected to the impedance measurement unit 130, and thus the output second voltage signal V_I may be transferred to the impedance measurement unit 130.

As described above, since the isolation transformer 52 and the Rogowski coil 53 are insulated from each other, the voltage-current measuring unit 50 has insulation characteristics. Therefore, the voltage-current measuring unit 50 may measure the voltage and current that do not affect the performance of the electrosurgical device 1 while using the same frequency as the operating frequency of the electrosurgical device 1 in consideration of the characteristics of the tissue.

Hereinafter, an embodiment of the impedance measurement unit 130 will be described with reference to FIG. 5.

Figure 5:
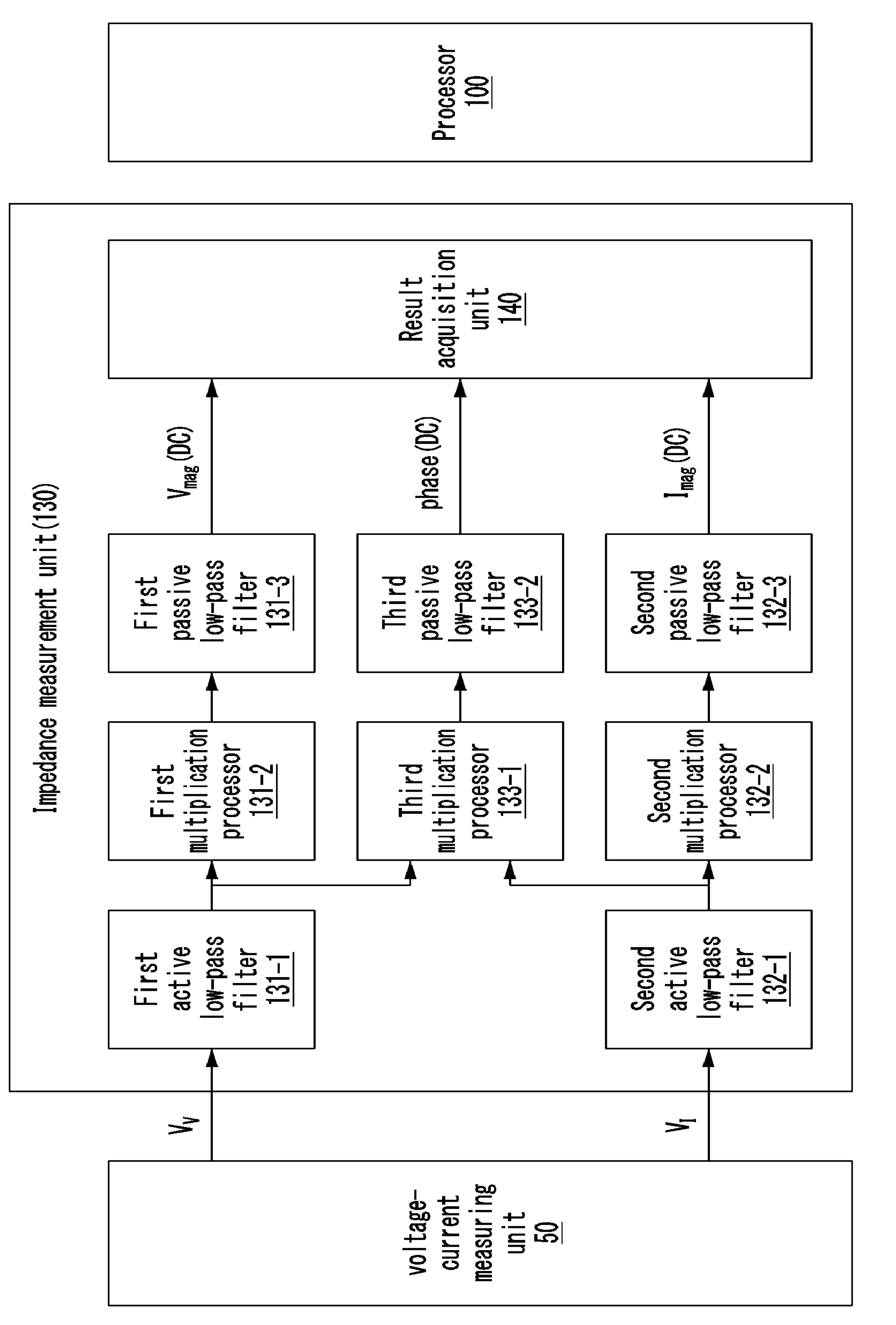
FIG. 5 is a block diagram of an impedance measurement unit according to an embodiment.

FIG. 5 is a block diagram of an impedance measurement unit according to an embodiment.

The impedance measurement unit 130 may measure an impedance of a target tissue, and may transmit a measurement result to the processor 100 so that the processor 100 may appropriately control energy supplied to the instrument 2. In detail, the impedance measurement unit 130 may convert the magnitude of the voltage, the magnitude of the current, and their phase information measured with respect to the high-frequency electrical signal into DC components, and may transfer the impedance information with respect to the high-frequency electrical signal to a result acquisition unit 140.

Referring to FIG. 5, in an embodiment, the impedance measurement unit 130 includes a first active low-pass filter 131-1 electrically connected to the voltage-current measuring unit 50, a first multiplication processor 131-2 connected in series to the first active low-pass filter 131-1, a first passive low-pass filter 131-3 connected in series to the first multiplication processor 131-2, a second active low-pass filter 132-1 electrically connected to the voltage-current measuring unit 50, a second multiplication processor 132-2 connected in series to the second active low-pass filter 132-1, a second passive low-pass filter 132-3 connected in series to the second multiplication processor 132-2, a third multiplication processor 133-1 connected to each of the first active low-pass filter 131-1 and the second active low-pass filter 132-1, a third passive low-pass filter 133-2 connected in series to the third multiplication processor 133-1, and may also include a result acquisition unit 140 that receives information from the first passive low-pass filter 131-3, the second passive low-pass filter 132-3, and the third passive low-pass filter 133-3.

The first active low-pass filter 131-1 receives the first voltage signal V_v from the voltage-current measuring unit 50, and the second active low-pass filter 132-1 receives the second voltage signal V_I from the voltage-current measuring unit 50. Here, the first voltage signal V_v and the second voltage signal V_I may be given by Equation 3 and Equation 4 below, respectively.

$$V_v = A \cos \omega t \quad \text{[Equation 3]}$$

$$V_I = B \cos (\omega t + \phi) \quad \text{[Equation 4]}$$

In Equation 3 and Equation 4, A denotes the magnitude of the first voltage signal V_v, B denotes the magnitude of the second voltage signal V_I, and φ denotes a phase difference between the signals V_v and V_I. That is, the second voltage signal V_I has a phase difference of a certain magnitude φ with respect to the first voltage signal V_v.

The first active low-pass filter 131-1 and the second active low-pass filter 132-1 may remove harmonic components from the received voltage signals V_v and V_I, respectively. In this case, the first active low-pass filter 131-1 and the second active low-pass filter 132-1 may remove harmonic components by allowing each of the voltage signals V_v and V_I to have a cutoff frequency lower than a second harmonic of a frequency to be measured. Accordingly, only a signal (e.g., a cosine signal) of a specific frequency is transferred to the first to third multiplication processors 131-2, 132-2, and 133-1.

The first to third multiplication processors 131-2, 132-2, and 133-1 include an analog circuit and perform multiplication on an input signal. For example, each of the first and second multiplication processors 131-2 and 132-2 may square a value received from the first active low-pass filter 131-1 or square a value received from the second active low-pass filter 132-1, and the third multiplication processor 133-1 may multiply a result of the first active low-pass filter 131-1 and a result of the second active low-pass filter 132-1. In other words, an output result of the first multiplication processor 131-2 may be given by Equation 5 below, an output result of the second multiplication processor 132-2 may be given by Equation 6 below, and an output result of the third multiplication processor 133-1 may be given by Equation 7 below.

$$A\cos\omega t \cdot A\cos\omega t = \frac{A^2}{2}(1 - \cos 2\omega t) \quad \text{[Equation 5]}$$

$$B\cos(\omega t + \phi) \cdot B\cos(\omega t + \phi) = \frac{B^2}{2}(1 - \cos(2\omega t + 2\phi)) \quad \text{[Equation 6]}$$

$$A\cos\omega t \cdot B\cos(\omega t + \phi) = \frac{AB}{2}(\cos\phi - \cos(2\omega t + \phi)) \quad \text{[Equation 7]}$$

In Equations 5 to 7, A, B, and φ are the magnitude of the first voltage signal V_v, the second voltage signal V_I, and the phase difference, respectively, as described above.

The first to third passive low-pass filters 131-3, 132-3, and 133-2 may receive the calculation results (signals) transmitted from the first to third multiplication processors 131-2, 132-2, and 133-1, respectively, acquire only the DC components V_mag(DC), I_mag(DC), and Phase(DC) necessary for impedance measurement information from the received corresponding signals, and transmit the acquired DC components V_mag(DC), I_mag(DC), and Phase(DC) to the result acquisition unit 140. In other words, the first passive low-pass filter 131-3 may obtain a DC component V_mag (DC) corresponding to a voltage, the second passive low-pass filter 132-3 may obtain a DC component I_mag(DC) corresponding to a current, and the third passive low-pass filter 133-2 may obtain a DC component Phase(DC) corresponding to a phase difference.

According to an exemplary embodiment, an output result of the first passive low-pass filter 131-3 may be given by Equation 8 below, an output result of the second passive low-pass filter 132-3 may be given by Equation 9 below, and an output result of the third passive low-pass filter 133-2 may be given by Equation 10 below.

$$V_{mag}(DC) = \frac{A^2}{2} \quad \text{[Equation 8]}$$

$$I_{mag}(DC) = \frac{B^2}{2} \quad \text{[Equation 9]}$$

$$\text{Phase}(DC) = \frac{AB}{2}\cos\phi \quad \text{[Equation 10]}$$

The result acquisition unit 140 may calculate and obtain a DC component more accurately based on the received voltage, current, and phase, and transfer the obtained result to the processor 100. For example, when an output result of the first passive low-pass filter 131-3 is given as shown in Equation 8, the result acquisition unit 140 may multiply the output result by 2 and calculate a square root to finally obtain the magnitude A of the voltage, and when an output result of the second passive low-pass filter 132-3 is transferred as shown in Equation 9, may multiply the output result by 2 and calculate a square root to finally obtain the magnitude B of the current. In addition, when the result acquisition unit 140 obtains the output result of the third passive low-pass filter 133-2 as shown in Equation 10, the magnitude of the voltage A and the magnitude of the current B obtained as described above are divided with respect to the obtained result, and an inverse trigonometric function operation is performed on the divided result, thereby obtaining information φ about the phase difference. Accordingly, it is possible to more accurately perform Analog to Digital Convert (ADC) on an analog signal. The result acquisition unit 140 may obtain an impedance corresponding to the high-frequency electrical signal based on the voltage A, the current B, and the phase difference φ, as necessary. The impedance may be transmitted to the processor 100. The result acquisition unit 140 may be implemented using, for example, a digital signal processor.

If analog-to-digital conversion is performed by transferring information of a voltage and a current measured for energy control to a digital signal processor without separate processing, unlike the above description, since a signal of a high frequency (for example, a 4 MHz signal) cannot be processed at a sampling frequency of a general digital signal processor, it is difficult to accurately perform energy control for a high frequency signal. On the other hand, since the impedance measurement unit 130 uses the PLL-based analog circuit as described above, the result acquisition unit 140, e.g., a digital signal processor, may accurately receive impedance information of a high frequency (e.g., 4 MHz), and accordingly, an accurate analog-to-digital conversion of an impedance of a high frequency may be possible.

The processor 100 and the impedance measurement unit 130 may be physically separated from each other, or may be logically separated from each other. When physically separated, the processor 100 and the impedance measurement unit 130 may be implemented using separate semiconductor chips and related circuit components, respectively, and when logically separated, the processor 100 and the impedance measurement unit 130 may be implemented using one semiconductor chip.

According to an embodiment, the impedance measurement unit 130 may be embedded in the electrosurgical device 1, or may be physically separated from the electrosurgical device 1, may be physically or electrically coupled to or separated from the electrosurgical device 1, and/or may be implemented using an impedance measuring device that can be independently driven. The impedance measuring device may be a device specifically designed to perform the operations illustrated in FIGS. 4 and 5.

Hereinafter, an embodiment of the energy control method will be described with reference to FIG. 6.

Figure 6:
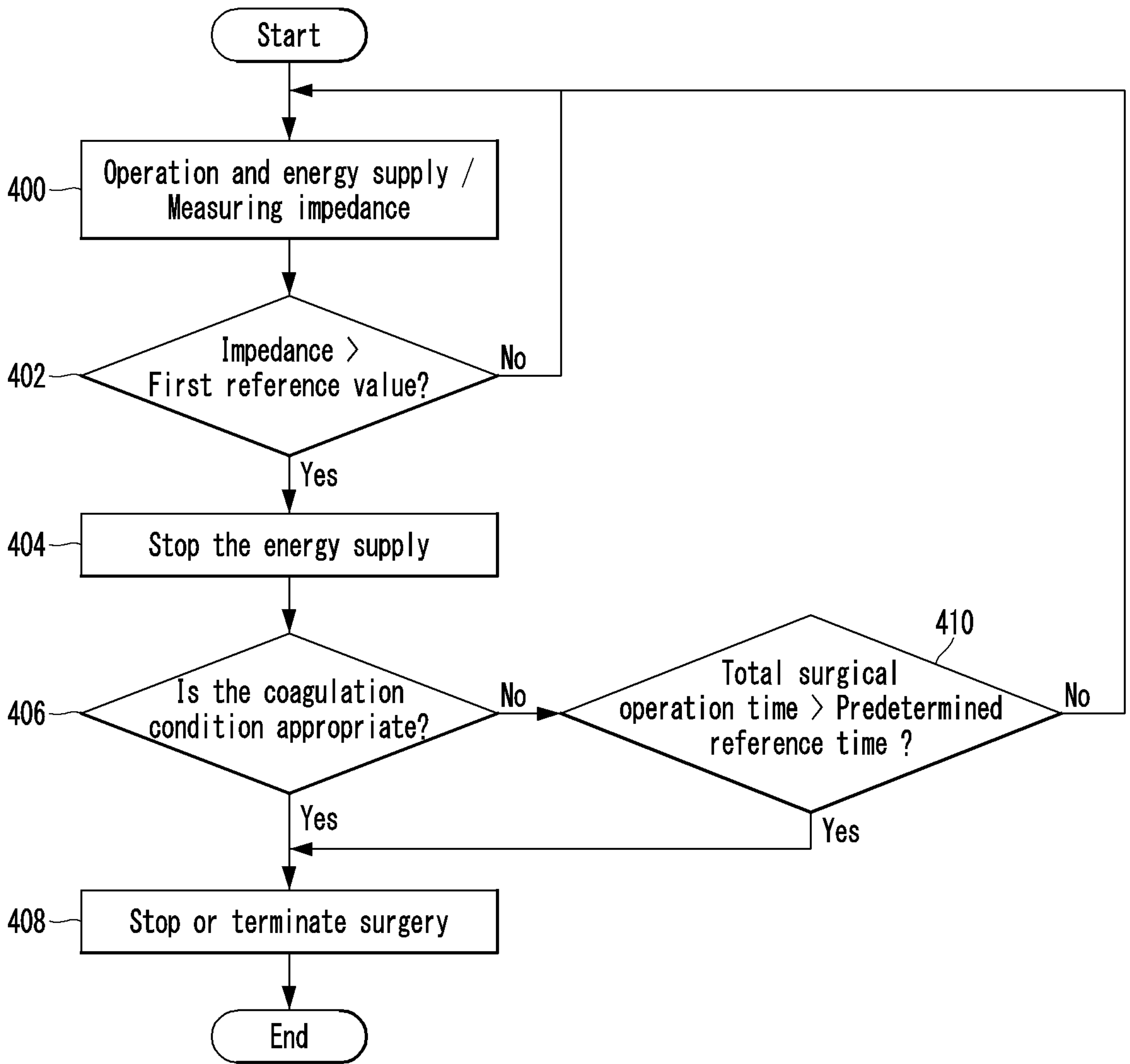
FIG. 6 is a flowchart of an embodiment of an energy control method.

FIG. 6 is a flowchart of an embodiment of an energy control method.

Figure 7:
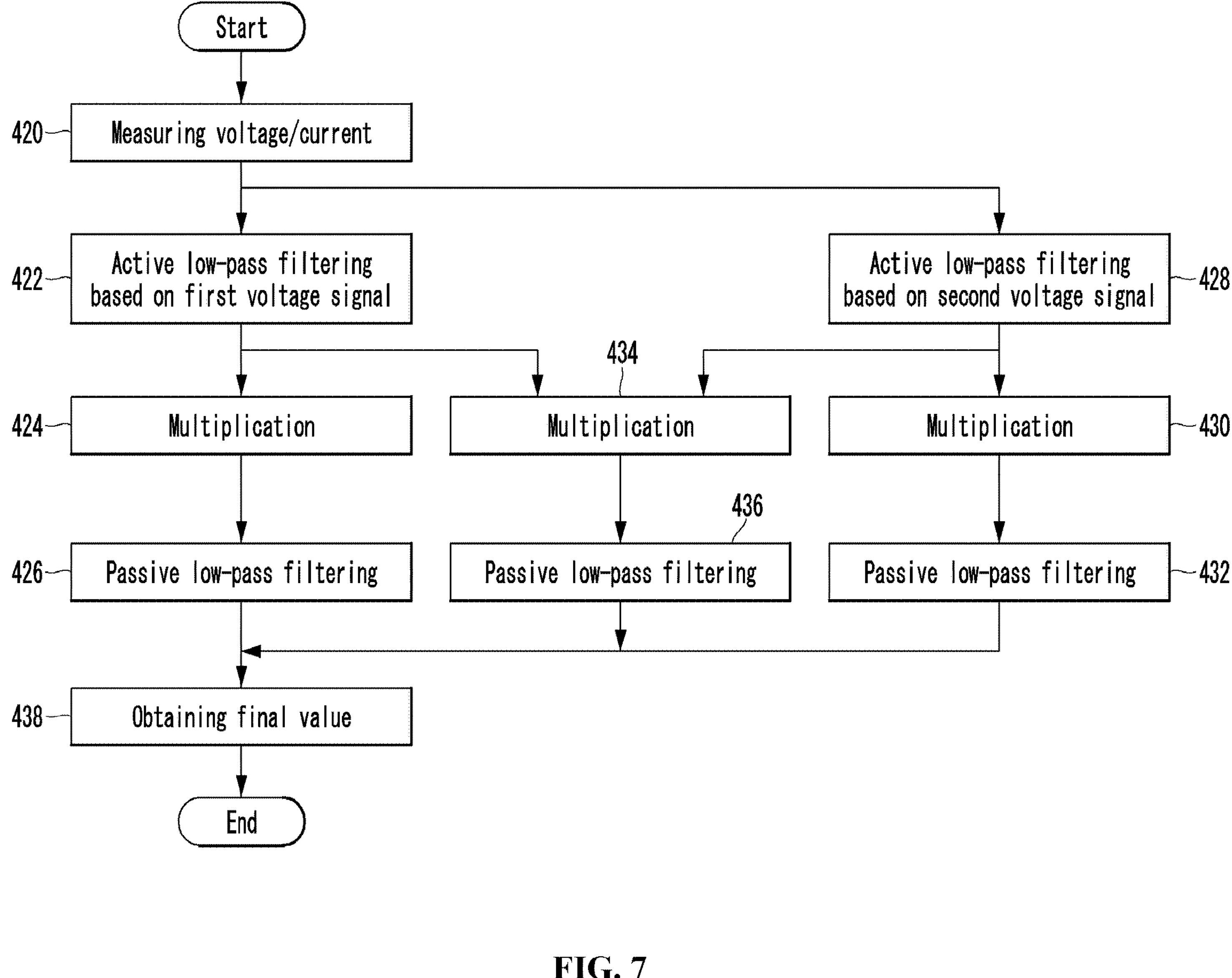
FIG. 7 is a flowchart illustrating an example of an impedance measuring method.

Referring to FIG. 6, an electrosurgical device operates, and energy is supplied to an instrument of the electrosurgical device (400). The energy supplied to the instrument may be performed with reference to at least one lookup table. The look-up table may be created by reflecting energy consumption according to parasitic resistance that greatly acts on a low impedance load, and for example, may be constructed by storing outputs transferred for each load through the tubing of the full bridge and the current measured by the instrument. The lookup table may include, for example, at least one of a lookup table for power and a lookup table for impedance. By controlling with reference to the lookup table, it is possible to accurately grasp and control the energy delivered to the organization. According to an embodiment, the impedance of the target tissue may be measured simultaneously or at different times with control of the supplied energy. The measurement of the impedance may be performed, for example, as illustrated in FIG. 7 to be described later.

The measured impedance is compared to a predefined first reference value (402). The first reference value may be predefined by a user or a designer to determine whether an impedance of the tissue is suitable for coagulation. When the impedance is less than the first reference value (NO of 402), the above-described energy supply operation and the impedance measurement operation may be continuously performed (400).

Conversely, when the impedance is greater than the first reference value (YES of 402), energy supply to the instrument is stopped (404). The interruption of the energy supply may be performed for a predefined time (e.g., 200 ms).

Then, the energy supply to the instrument may be resumed, an impedance may be additionally measured, and a coagulation state may be determined using the measured impedance (406). When the energy supply is stopped, moisture around the target tissue is introduced into the target tissue, and thus the measured impedance has a relatively smaller value than the impedance before the energy supply. Therefore, the moisture amount of the surrounding tissue may be measured based on the measured impedance (for example, the value of the minimum impedance recorded when energy is applied), and the coagulation state may be determined based on the moisture amount.

If it is determined that the coagulation state is appropriate because the impedance is greater than the second reference value (YES in 406), it is determined that the coagulation of the incised target tissue and/or the surrounding tissue is completed, and the surgery is stopped or terminated (408).

Conversely, when the impedance is less than the second reference value and thus the coagulation state is not determined to be appropriate (NO of 406), it may be sequentially determined whether the total surgical operation time exceeds a predetermined reference time (e.g., 10 sec) (410). If the total operation time exceeds the predetermined reference time (YES of 410), the energy supply to the instrument is terminated to prevent an unexpected accident, and the operation is terminated or stopped (408). On the contrary, if the total operation time does not exceed the predetermined reference time (YES of 410), energy supply to the instrument may be continuously performed, and operations 400 to 406 of receiving impedance, stopping energy supply, and determining whether a coagulation state is appropriate may be repeatedly performed.

Hereinafter, an embodiment of an impedance measuring method will be described with reference to FIG. 7.

FIG. 7 is a flowchart illustrating an example of impedance measuring method.

In an embodiment, the above-described impedance measurement process 400 may be performed as illustrated in FIG. 7. The measurement of the impedance may be obtained by calculating based on the voltage and current output from the instrument.

First, the output voltage and current are measured (420). The measurement of the voltage and the current may be performed using the voltage-current measuring unit 50 illustrated in FIG. 4. A first voltage signal corresponding to the voltage is transmitted through capacitor 51 and isolation transformer 52, and a second voltage signal corresponding to the current is transmitted through PCB Rogowski coil 53 and active integrator 54.

The first voltage signal may be given by Equation 3, which is filtered through an active low-pass filter (422), multiplied by Equation 5 (424), and filtered through a passive low-pass filter (426). Accordingly, an output result (i.e., a DC component corresponding to a voltage) as shown in Equation 8 is obtained.

The magnitude of the voltage may be finally obtained by dividing the DC component corresponding to the voltage and calculating the square root (438).

The second voltage signal may be given as in Equation 4 described above, and is filtered through the active low-pass filter (428), and then multiplied to obtain a result of the multiplication process as given in Equation 6 (430), and then the result of the multiplication process is filtered through the passive low-pass filter (432). Accordingly, a direct current component corresponding to the current may be obtained, for example, as shown in Equation 9.

Similarly, the magnitude of the current may be finally obtained from the DC component corresponding to the current by using a square root operation or the like (438).

Meanwhile, the active low-pass filtering result for the first voltage signal and the active low-pass filtering result for the second voltage signal are multiplied as shown in Equation 7 (434), and the processing result is filtered while passing through the passive low-pass filter (436). Accordingly, a direct current component corresponding to a phase is obtained as shown in Equation 10.

An inverse cosine operation is performed on the DC component corresponding to the phase, and accordingly, a phase may be finally obtained (438).

Accordingly, a voltage, a current, and a phase can be more accurately obtained with respect to a high frequency signal, and a digital signal of an analog signal can be more accurately converted.

At least one of the energy control method and the impedance measurement method described in the aforementioned embodiments can be implemented in the form of a program that can be executed by a computer device. The program may include instructions, libraries, data files, and/or data structures, either individually or in combination, and can be designed and produced using either machine code or high-level language code. The program could be specifically designed to implement the described method, or it could be implemented using various functions or definitions that are already known and available to those skilled in the art within the field of computer software. Additionally, the computer device mentioned here may be implemented by including a processor or memory that enables the functionality of the program and may further include a communication device if necessary. Moreover, a program for implementing at least one of the described energy control method and impedance measurement method can be recorded on a recording medium readable by a device, such as a computer. Recording media that can be read by a computer include, for example, semiconductor storage media such as ROM, RAM, SD cards, or flash memory (e.g., solid-state drives (SSD)), magnetic disk storage such as hard disks or floppy disks, optical recording media such as compact discs or DVDs, or magneto-optical recording media such as floptical disks. It may encompass any type of physical storage medium capable of temporarily or permanently storing one or more programs that are executed upon call from a device, such as a computer.

Although several embodiments of the electrosurgical device, the impedance measuring device for the electrosurgical device, the energy control method for tissue coagulation, and the impedance measurement method have been described, the electrosurgical device, the impedance measuring device for the electrosurgical device, and the energy control method or impedance measurement method for tissue coagulation are not limited to the described embodiment(s). Various other devices or methods that can be implemented by those skilled in the art by modifying and altering the described embodiments based on the principles outlined may also constitute embodiments of the described electrosurgical device, the impedance measuring device for the electrosurgical device, the energy control method for tissue coagulation, or the impedance measurement method. For example, the described method(s) may be executed in an order different from that described, and/or component(s) of the described system, structure, device, circuit, etc., may be combined, connected, or otherwise arranged in a form different from that described. Even if combined or replaced with other components or equivalents, it could still be considered an embodiment of the described electrosurgical device, the described impedance measuring device, the energy control method for tissue coagulation, and/or the impedance measurement method.

INDUSTRIAL APPLICABILITY

The present invention relates to an electrosurgical device and an energy control method for tissue coagulation, which appropriately controls energy supply to a target tissue and the like in a surgical process, thereby preventing the target tissue or surrounding tissue of the target tissue from being damaged by heat while the target tissue is properly coagulated, operating an electrosurgical device based on high frequency energy, determining high frequency energy required for tissue coagulation based on impedance measured in real time, applying the determined high frequency energy to the tissue, appropriately measuring the impedance of the target tissue or surrounding tissue in a high frequency band, more appropriately controlling the energy supply to the target tissue and the like based on the measured impedance, measuring the impedance in the high frequency band, which was impossible to measure due to a sampling frequency limitation of a conventional Digital Signal Processor (DSP), by performing a calculation process based on the conventional Pulse Lock Loop (PLL) through an analog circuit, and measuring the impedance without deteriorating the performance of the electrosurgical device by minimizing electrical interference to the electrosurgical device, thereby having high industrial applicability.

[Description of signs]

| | |
|---|---|
| 1: electrosurgical device | 10: energy supply unit |
| 50: voltage-current measuring unit | 90: storage unit |
| 91: lookup table | 100: processor |
| 110: output controller | 120: impedance receiving unit |
| 121: coagulation determining unit | 122: moisture amount determining unit |
| 130: impedance measurement unit | 140: result acquisition unit |

The invention claimed is:

1. An electrosurgical device, the device comprising:

an instrument for surgery on a target tissue;

a processor configured to control energy supply to the instrument;

an impedance measurement circuit configured to measure an impedance of the target tissue;

a voltage-current measuring circuit; and wherein the processor is further configured to stop the energy supply to the instrument during a stop period when the impedance measured by the impedance measurement circuit exceeds a first reference value, resume the energy supply to the instrument after the stop period has elapsed, and determine a coagulation state based on the impedance of the target tissue measured after the resumption of the energy supply by the impedance measurement circuit, wherein the voltage-current measuring circuit comprises:

a capacitor;

an isolation transformer connected to the capacitor and configured to output a first voltage signal corresponding to a voltage;

a PCB Rogowski coil installed adjacent to a conducting wire to which the capacitor is connected; and an active integrator connected to the PCB Rogowski coil and configured to correct a phase of the active integrator to output a second voltage signal corresponding to a current, and wherein the impedance measurement circuit comprises:

a first active low-pass filter configured to remove a harmonic component of the first voltage signal, the first active low-pass filter having a cutoff frequency lower than a second harmonic of a frequency to be measured such that the harmonic component is removed;

a first multiplication processor configured to perform a multiplication process on an output of the first active low-pass filter;

a first passive low-pass filter configured to obtain a direct current component corresponding to a voltage from a result of the first multiplication processor;

a second active low-pass filter configured to remove a harmonic component of the second voltage signal, the second active low-pass filter having a cutoff frequency lower than a second harmonic of a frequency to be measured such that the harmonic component is removed;

a second multiplication processor configured to perform a multiplication process on an output of the second active low-pass filter;

a second passive low-pass filter configured to obtain a direct current component corresponding to a current from a result of the second multiplication processor;

a third multiplication processor configured to perform a multiplication process on an output of the first active low-pass filter and the second active low-pass filter;

a third passive low-pass filter configured to obtain a direct current component corresponding to a phase from a result of the third multiplication processor; and a result acquisition processor configured to determine a voltage and a current, based on the direct current component corresponding to the voltage and the direct current component corresponding to the current, to determine a phase by dividing the direct current component corresponding to the phase by a magnitude of the voltage and a magnitude of the current and performing an inverse trigonometric function operation on a result of the division, and to determine an impedance based on the voltage, the current, and the phase.

2. The electrosurgical device of claim 1, wherein the processor is configured to control the energy supply to the instrument using at least one lookup table.

3. The electrosurgical device of claim 1, wherein the processor is further configured to determine a moisture amount of surrounding tissues of the target tissue by using the impedance of the target tissue measured by the impedance measurement circuit after the energy supply is resumed, and determine the coagulation state based on the moisture amount.

4. The electrosurgical device of claim 1, wherein the processor is configured to block the energy supply to the instrument when a total surgical time exceeds a reference time.

5. An electrosurgical method, the method comprising:

supplying energy to an instrument for surgery of a target tissue;

measuring an impedance of the target tissue;

stopping the energy supply to the instrument during a stopping period when the impedance measured by the impedance measuring circuit exceeds a first reference value;

resuming the energy supply to the instrument after the stopping period has elapsed; and determining a coagulation state based on the impedance of the target tissue measured after resuming the energy supply, wherein the measuring an impedance of the target tissue comprises:

measuring a voltage and a current; and obtaining an impedance based on a first voltage signal and a second voltage signal, wherein the voltage and the current are measured by using a voltage-current measuring circuit, wherein the voltage-current measuring circuit comprises:

a capacitor;

an isolation transformer connected to the capacitor and outputting the first voltage signal corresponding to the voltage;

a PCB Rogowski coil installed adjacent to a conducting wire to which the capacitor is connected; and an active integrator connected to the PCB Rogowski coil and correcting a phase to output the second voltage signal corresponding to the current, and wherein the obtaining an impedance based on the first voltage signal and the second voltage signal comprises:

p2 removing a harmonic component from each of the first voltage signal and the second voltage signal, by allowing each of the voltage signals to have a cutoff frequency lower than a second harmonic of a frequency to be measured;

performing multiplication on each of the first voltage signal from which the harmonic component is removed and the second voltage signal from which the harmonic component is removed;

obtaining a direct current component corresponding to a voltage and a direct current component corresponding to a current from each multiplication result;

performing multiplication by using both the first voltage signal from which the harmonic component is removed and the second voltage signal from which the harmonic component is removed;

obtaining a direct current component corresponding to a phase from a multiplication result using both the first voltage signal from which the harmonic component is removed and the second voltage signal from which the harmonic component is removed;

determining a voltage and a current, based on the direct current component corresponding to the voltage and the direct current component corresponding to the current;

determining a phase by dividing the direct current component corresponding to the phase by a magnitude of the voltage and a magnitude of the current and performing an inverse trigonometric function operation on a result of the division; and determining the impedance based on the voltage, the current, and the phase.

6. The electrosurgical method of claim 5, wherein the supplying energy to an instrument for surgery of a target tissue comprises:

supplying energy to the instrument for the surgery of the target tissue using at least one lookup table.

7. The electrosurgical method of claim 5, wherein the determining the coagulation state based on the impedance of the target tissue measured after resuming the energy supply comprises:

determining a moisture amount of surrounding tissue of the target tissue by using the impedance of the target tissue measured after the energy supply resumption; and determining the coagulation state based on the moisture amount around the target tissue.

8. The electrosurgical method of claim 5, further comprising:

blocking the energy supply to the instrument when a total surgical time exceeds a reference time.

* * * * *